US009420950B2

(12) United States Patent
Gao et al.

(10) Patent No.: US 9,420,950 B2
(45) Date of Patent: Aug. 23, 2016

(54) RETRO-REFLECTIVITY ARRAY FOR ENABLING PUPIL TRACKING

(71) Applicant: AVAGO TECHNOLOGIES GENERAL IP (SINGAPORE) PTE. LTD., Singapore (SG)

(72) Inventors: Jun Gao, Hsin-Chu (TW); Raimund Ortiz, Hsin-Chu (TW); Julie Fouquet, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 331 days.

(21) Appl. No.: 14/028,542

(22) Filed: Sep. 17, 2013

(65) Prior Publication Data

US 2015/0077313 A1 Mar. 19, 2015

(51) Int. Cl.
*G06K 9/00* (2006.01)
*A61B 3/113* (2006.01)
*G02B 27/00* (2006.01)
*G06F 3/01* (2006.01)

(52) U.S. Cl.
CPC ............ *A61B 3/113* (2013.01); *G02B 27/0093* (2013.01); *G06F 3/013* (2013.01)

(58) Field of Classification Search
USPC .................................. 382/115–118, 124–127
See application file for complete search history.

(56) References Cited

U.S. PATENT DOCUMENTS

| 5,054,907 | A | 10/1991 | Sklar |
| 7,522,344 | B1 | 4/2009 | Curatu |
| 7,747,068 | B1* | 6/2010 | Smyth .................... G03B 17/00 382/154 |
| 8,322,856 | B2 | 12/2012 | Vertegaal |
| 2002/0057846 | A1* | 5/2002 | Saitou ................ H04N 1/02815 382/274 |
| 2005/0105047 | A1 | 5/2005 | Smitth, III |
| 2006/0093998 | A1 | 5/2006 | Vertegaal |
| 2012/0212598 | A1* | 8/2012 | Mowrey ................... A61B 3/14 348/78 |

FOREIGN PATENT DOCUMENTS

| CN | 2438423 Y | 7/2001 |
| CN | 101295355 A | 10/2008 |
| CN | 101566727 A | 10/2009 |
| CN | 102955255 A | 3/2013 |
| TW | 201241678 A1 | 10/2012 |
| TW | 201314263 | 4/2013 |
| WO | 2012098325 A2 | 7/2012 |

\* cited by examiner

*Primary Examiner* — Alex Liew
(74) *Attorney, Agent, or Firm* — Winston Hsu; Scott Margo

(57) ABSTRACT

An optical array system for performing pupil tracking using retro-reflectivity includes: an LED array including at least one on-axis LED and at least one off-axis LED, for illuminating pupils of a user within an active region; a high-speed camera with a gaming motion sensor, for capturing images of the pupils illuminated by the LED array; and a processor, coupled to the high-speed camera, for receiving the captured images and performing processing algorithms on them to isolate pupil information and thereby determine pupil presence and location within the active region.

18 Claims, 7 Drawing Sheets

RETRO-REFLECTIVITY ARRAY FOR ENABLING PUPIL TRACKING

BACKGROUND OF THE INVENTION

1. Field of the Invention

The present invention relates to a retro-reflectivity array, and more particularly, to a retro-reflectivity array comprising a camera with a high speed sensor which can perform pupil tracking.

2. Description of the Prior Art

Retro reflectivity is a property of the human eye, meaning that when a light source is shone into the eye, a majority of the incident light will be reflected back in the direction from which it came. This property gives rise to what is commonly known as the 'red-eye effect' in photographs. An optical axis can be imagined as a line running between the centre of an imager, such as a camera, and the centre of the pupil of a human eye. In order for the eye's retro-reflective properties to be detected, the light source shining into the eye should be located next to the imager (on-axis) so that the pupil reflects the light back towards the source. Then it will show up as a bright spot. When the light source is located away from the imager (off-axis), the retro-reflection from the pupil will miss the imager and the pupil will appear dark in the image.

By using this red-eye effect, both the presence and location of a person's eyes can be determined. Please refer to FIG. 1, which is a diagram illustrating a system 100 for performing pupil detection according to the related art. A human eye 50 is positioned opposite an imager 30. LED arrays 15, 13 are placed either side of the imager 30. The LED array 15 comprises an on-axis LED 2 and an off-axis LED 7; the LED array 13 comprises an on-axis LED 4 and an off-axis LED 9. Certain calibration procedures will be performed to determine the on-axis illumination angle and the off-axis illumination angle, wherein the on-axis illumination angle can be calibrated by the imager 30 detecting reflected light from the pupils above a certain threshold, and the off-axis illumination angle can be calibrated by the imager 30 capturing an image with completely dark pupils. By differencing the two images, only the pupil information will remain. It is therefore possible to determine for what percentage of time the user's eyes are open or visible to the imager (e.g. the person has not turned around). Retro-reflection will be viewed from the pupil regardless of gaze angle in any configuration where the LED is near the imager and the pupil is visible.

One application of this technology is detailed in U.S. Pat. No. 7,280,678. A retro-reflectivity array similar to that illustrated in FIG. 1 is used to detect when a driver of a car is falling asleep. Because the driver should be looking ahead at the road, the driver's gaze angle should be relatively fixed. By setting a threshold which takes into account occasional glances over the shoulder as well as blinking, the pupils should be able to be detected for a certain percentage of time above that threshold value. When the pupil detection falls below the threshold value, this indicates that the driver is falling asleep (or distracted) and an alarm or similar warning system can be activated.

This technology is limited by the speed of a conventional sensor and processor used in such applications, which allow image frames to be caught and processed at less than 60 frames per second. At these speeds, it is possible to determine the presence of pupils, i.e. whether or not a user is alert. However, if the subject is moving quickly, both the on-axis and off-axis images must be collected simultaneously using specialized optical filters. Although the differenced images of the concept described above are able to successfully detect pupils, the present invention aims to explore an alternative method of implementation using an image-based approach with a high-speed camera to detect pupils. In this case, the frame rate is so high that the on-axis and off-axis frames can be collected one after the other without requiring specialized optical filters.

SUMMARY OF THE INVENTION

With this in mind, it is therefore an objective of the present invention to provide an optical array for using retro reflectivity to perform pupil tracking.

An optical array system for performing pupil tracking using retro-reflectivity comprises: an LED array comprising at least one on-axis LED and at least one off-axis LED, for illuminating pupils of a user within an active region; a high-speed camera with a gaming motion sensor, for capturing images of the pupils illuminated by the LED array; and a processor, coupled to the high-speed camera, for receiving the captured images and performing processing algorithms on them to isolate pupil information and thereby determine the presence of pupils within the active region.

A method for performing pupil tracking using retro-reflectivity comprises: illuminating pupils of a user within an active region utilizing at least one on-axis LED and at least one off-axis LED; providing a high-speed camera with a gaming motion sensor for capturing images of the illuminated pupils; and receiving the captured images and performing processing algorithms on the captured images to isolate pupil information and thereby determine the presence of pupils within the active region.

These and other objectives of the present invention will no doubt become obvious to those of ordinary skill in the art after reading the following detailed description of the preferred embodiment that is illustrated in the various figures and drawings.

DETAILED DESCRIPTION

The present invention provides an optical array which can detect pupil presence and location at high speed, thereby enabling pupil tracking and, in certain situations, gaze tracking. One implementation of this system is as a human interface device.

The main inventive concept of the proposed optical array is to employ a high-speed, low resolution camera for capturing pupil images that uses a mouse navigation sensor, such as those used in gaming. In contrast with conventional cameras utilized in retro-reflectivity applications, the camera using a mouse navigation sensor can capture and process images at a high frame rate, thereby allowing pupil presence, location and movement to be detected. As the camera can ascertain different locations of the pupil, tracking algorithms can be determined and employed for performing pupil tracking within a certain defined area known as an active area.

Figure 1:
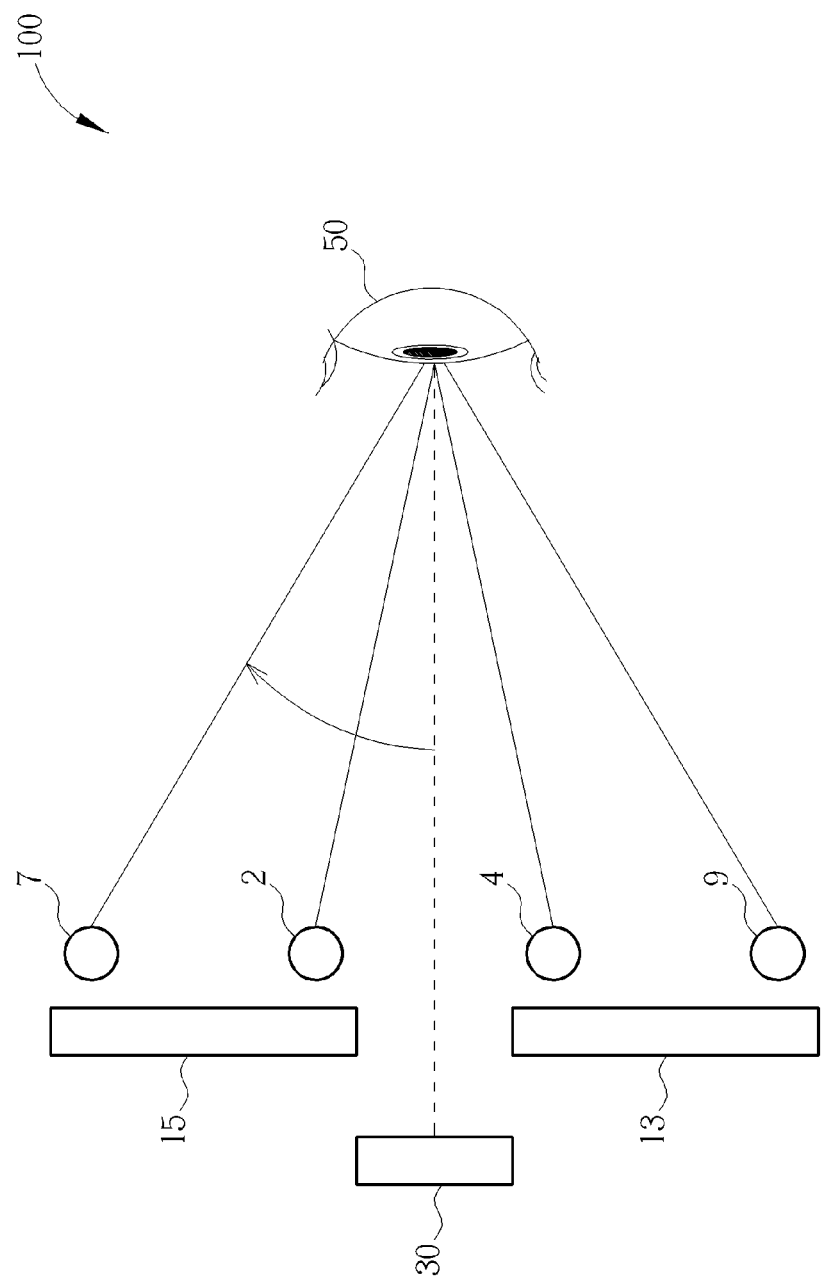
FIG. 1 is a diagram illustrating a light source being shone into a human eye both at an on-axis illumination angle and at an off-axis illumination angle, for an axis defined between the imager and the eye.
Figure 2A:
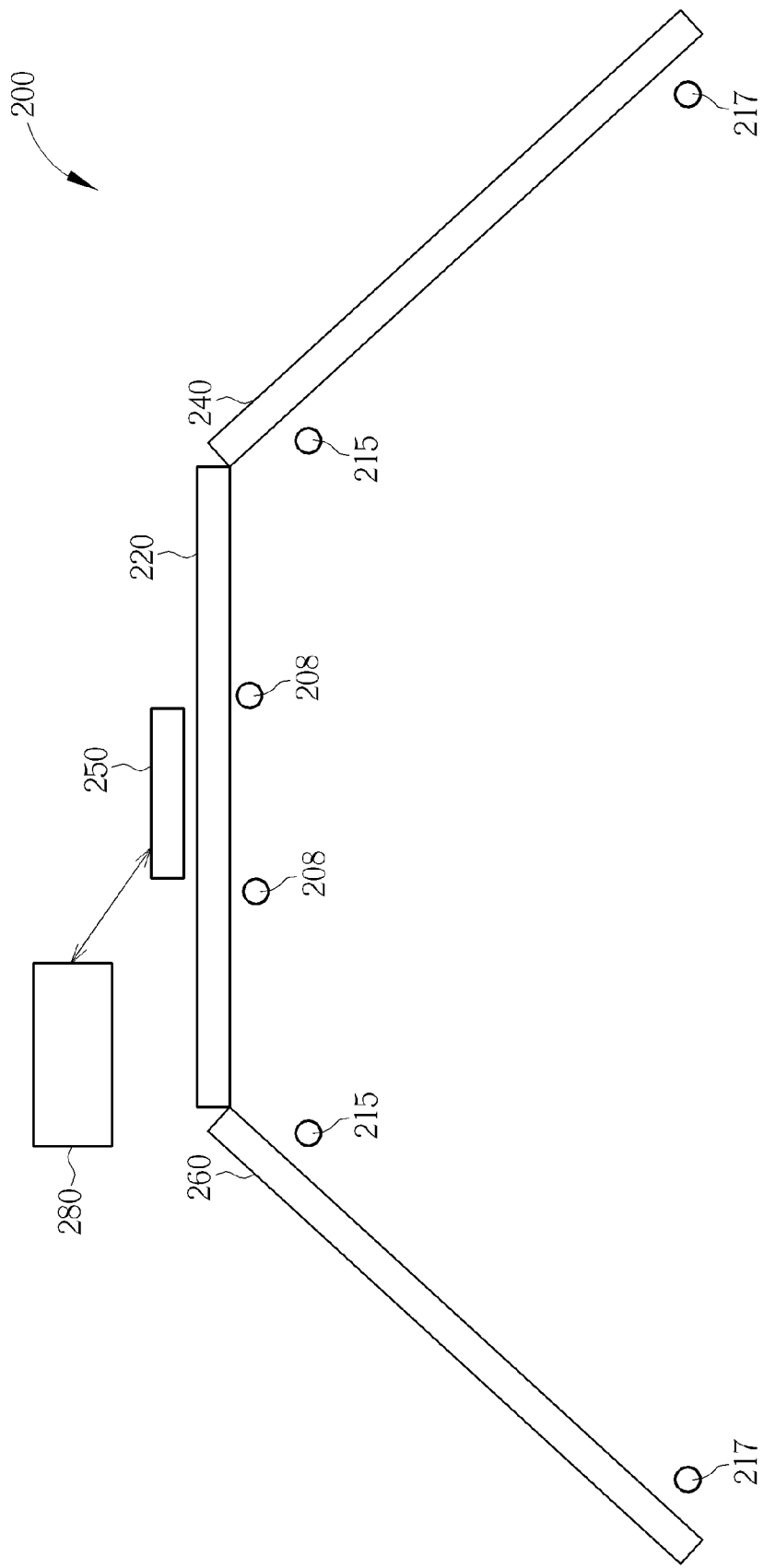
FIG. 2A illustrates a plan view of an optical array according to a first embodiment of the present invention.
Figure 2B:
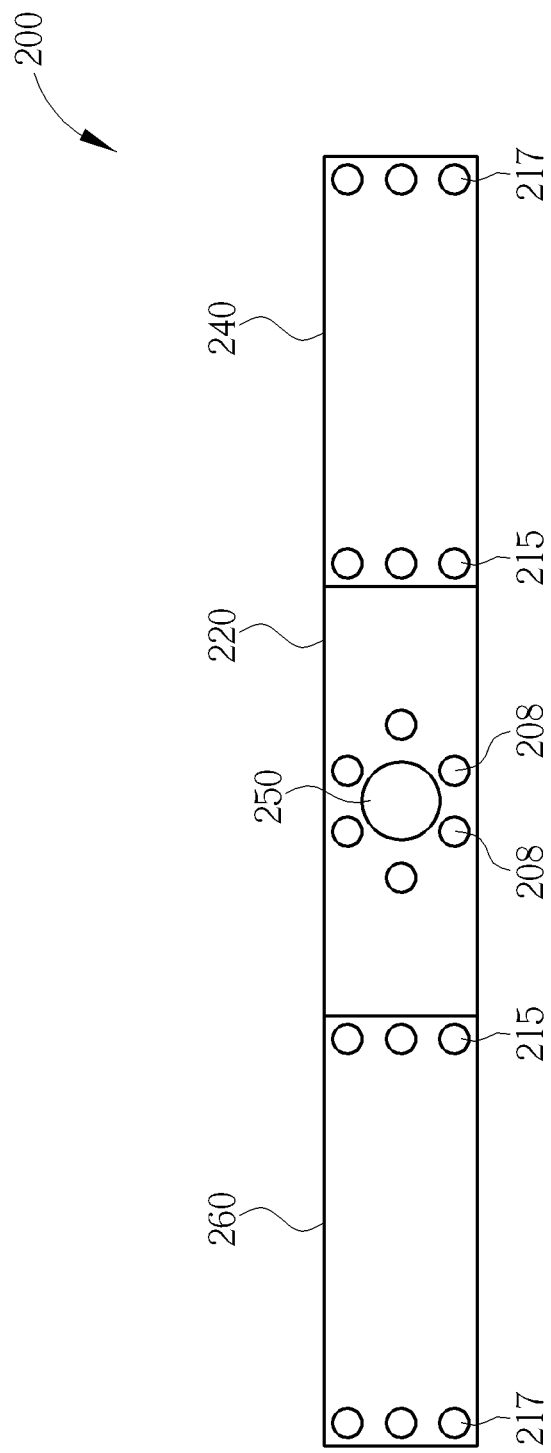
FIG. 2B illustrates a face-on view of the optical array illustrated in FIG. 2A.

Please refer to FIG. 2A, which illustrates a plan view of an optical array 200 according to a first embodiment of the present invention, and to FIG. 2B, which illustrates the optical array 200 face-on. As shown in the diagrams, the optical array 200 is three-sided, consisting of a left-hand panel 260, a centre panel 220 and a right-hand panel 240. The high-speed, low resolution camera 250 is placed in the middle of the centre panel 220. A USB connector (not shown) attached to the camera 250 provides a USB signal to a high-speed image data acquisition application in a processor 280, which can process captured images for performing tracking and gaze detection. In FIG. 2A, the left-hand panel 260 and right-hand panel 240 are both placed at a 148 degree angle with respect to the centre panel 220 but this is merely one implementation.

LEDs placed on the panels of the optical array 200 form a series of sections of illumination rings for enabling on-axis and off-axis illumination. A middle ring 208 is formed of 6 LEDs (as illustrated in FIG. 2B), which surround the camera. Please note this figure is merely given as an example. These LEDs form a middle ring of the array. 6 LEDs are also respectively disposed on the left-hand panel 260 and the right-hand panel 240, wherein 3 of the LEDs are directly next to the centre panel, forming ring 215, and the remaining 3 of the LEDs are on the outermost edge, forming an outer ring 217. Please note that other LEDs can be placed on any of the panels of the optical array system 200 for providing a more versatile arrangement; the LEDs illustrated in FIG. 2 are merely one embodiment of the invention.

The following will detail how images are captured and processed. Initially, the system 200 will need to be calibrated to find the correct on-axis and off-axis illumination angles, and also to fix a user's approximate height and distance from the array 200. Within the parameters of the camera lens, which is crucial for setting an 'active region', the active region is further defined by using standardized body dimensions in order to set an average eye height while sitting and by using an average distance between pupils. These two parameters respectively set the y and x axes of the active region. The camera 250 also needs to be capable of responding to a minimum frequency which is defined as a velocity at which the head may move. The illumination level of the inner ring 208 and the outer rings 215 and 217 can also be calibrated. This sets an area in which the camera 250 can detect pupil presence and location, which will be the active area.

Images are captured by the camera and down-sampled, wherein the time difference between each down-sampled frame may be approximately 5.0 ms or less. The off-axis and on-axis illuminated images are differenced to isolate the pupil information. The difference image can then be evaluated by a tracking algorithm. With this isolated pupil information, the processor can quickly determine whether the person is alert. The high speed of the mouse navigation sensor enables quick reaction times between the movement of the user's eyes and the feedback from the processor. In order to further remove background noise, a threshold pixel value is applied to the differenced frames. This threshold pixel value filters out the background noise, leaving only the highlighted pupils.

The standard way to determine gaze direction is to compare the location of the (large) pupil with the location of the specular reflection off the surface of the eye. When a user's gaze can constantly be tracked, the optical array system can be implemented as a Human Interface Device (HID). The previously-discussed low-resolution high-speed camera located far from the user cannot collect this fine scale information, however.

Figure 3A:
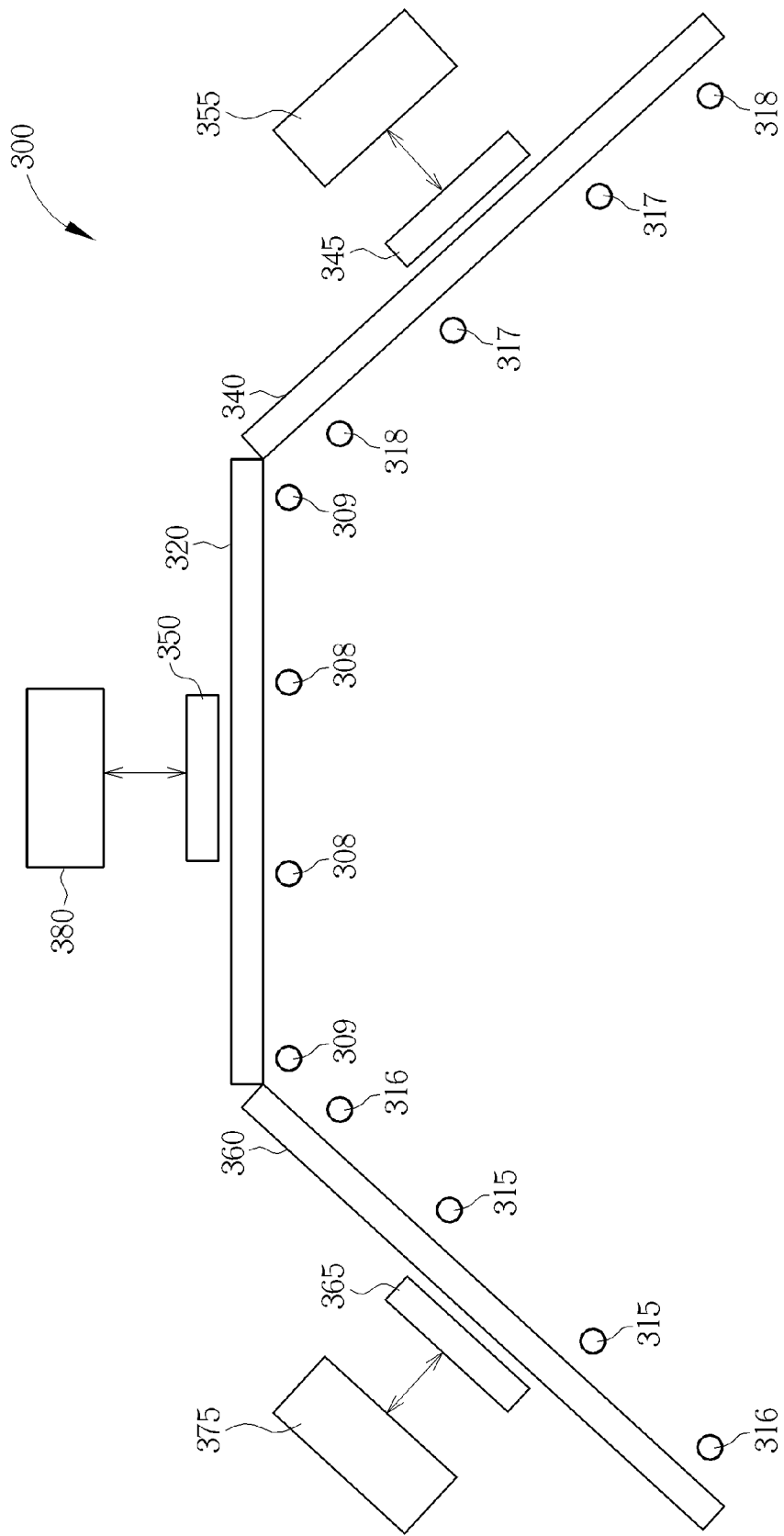
FIG. 3A illustrates a plan view of an optical array according to a second embodiment of the present invention.
Figure 3B:
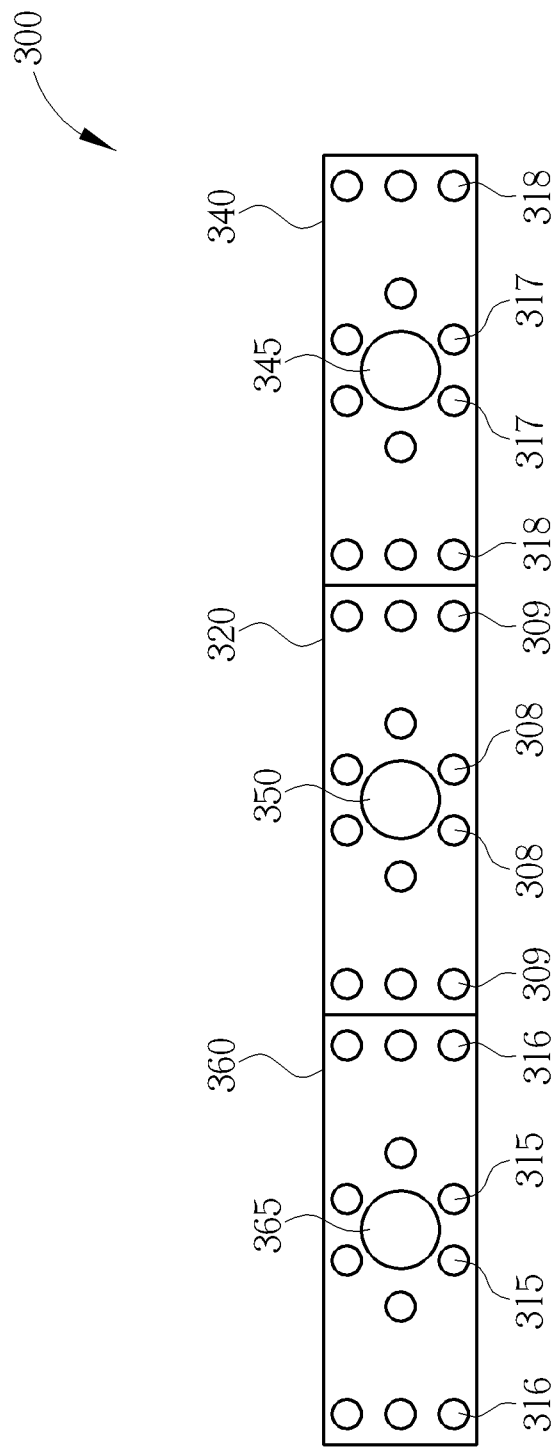
FIG. 3B illustrates a face-on view of the optical array illustrated in FIG. 3A.

A second embodiment of the present invention is illustrated in FIGS. 3A and 3B. FIG. 3A illustrates a three-sided optical array 300, consisting of a left-hand panel 360, a centre panel 320 and a right-hand panel 340. In this embodiment, all three panels of the optical array are provided with a high-speed, low resolution camera. A high-speed, low resolution camera 365 is placed in the middle of the left-hand panel 360; a high-speed, low resolution camera 350 is placed in the middle of the centre panel 320; and a high-speed, low resolution camera 345 is placed in the middle of the right-hand panel 340. USB connectors (not shown) attached to the cameras 365, 350, 345 respectively provide USB signals to a high-speed image data acquisition application in processors 375, 380, 355, which can process captured images for performing tracking and gaze detection.

As illustrated in FIG. 3B, each camera is respectively surrounded with an inner ring and a partial outer ring of LEDs. For example, camera 365 is surrounded with an inner ring of LEDs 315 and a partial outer ring of LEDs 316. Camera 350 is surrounded with an inner ring of LEDs 308 and a partial outer ring of LEDs 309. Camera 345 is surrounded with an inner ring of LEDs 317 and a partial outer ring of LEDs 318. In this second embodiment, the high-speed, low resolution cameras 365, 350, 345 are fired sequentially and in rapid succession. Differential images are obtained from each camera and compared using an algorithm. These comparison algorithms will give information about pupil shape and brightness, which can be used to determine a coarse gaze direction. If the eye is pointed towards one of the high-speed, low resolution cameras 365, 350, 345, the pupil will appear bright and approximately circular. If the eye is pointed somewhat away from a camera, the pupil will appear dimmer and less round. If the direction of the gaze is at a great enough angle from the camera, the pupil will not appear at all.

Figure 4A:
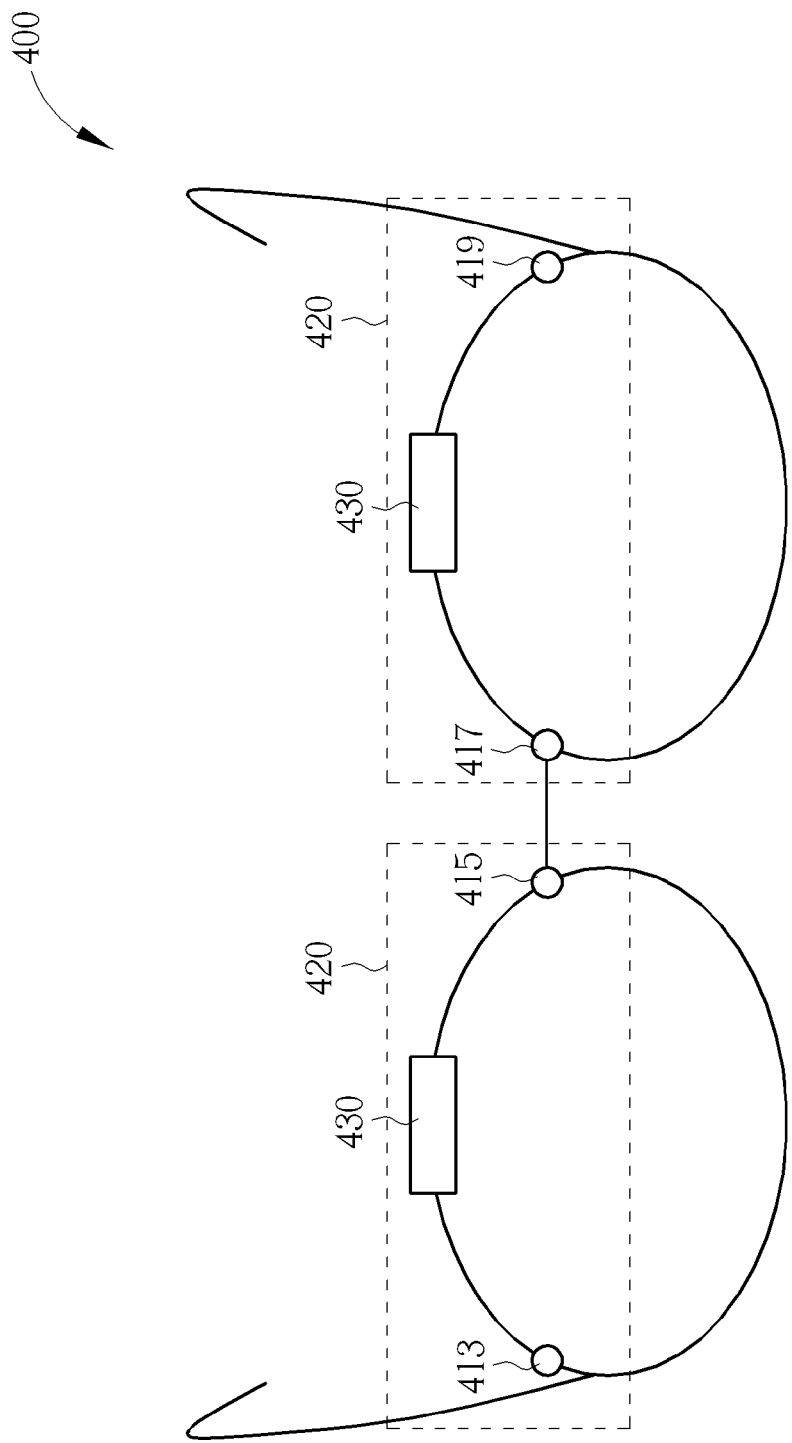
FIG. 4A is a diagram of one implementation of the present invention according to an exemplary embodiment of the present invention.
Figure 4B:
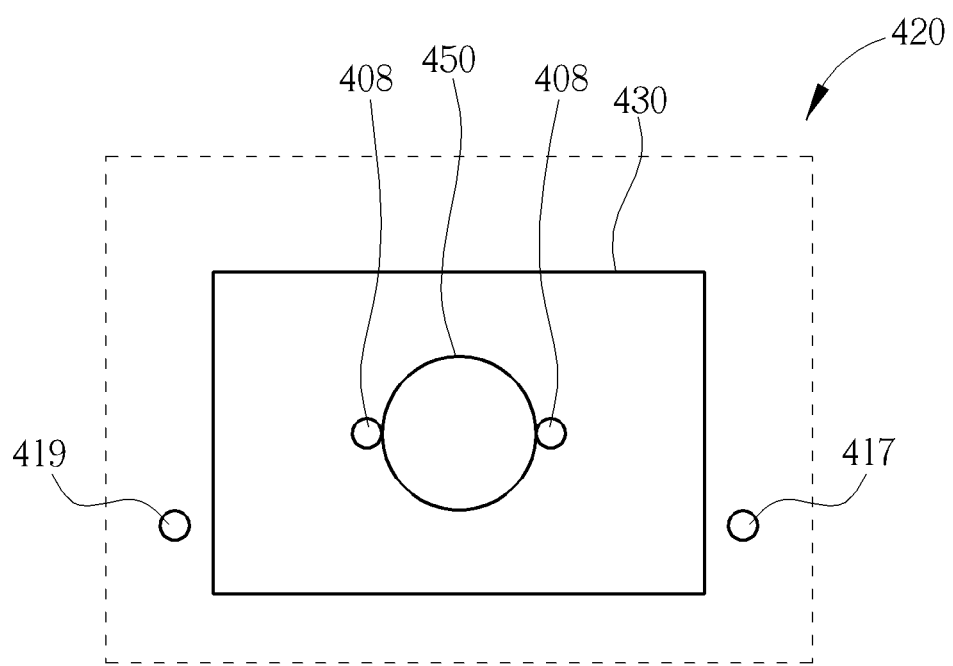
FIG. 4B is a diagram of an optical array of the exemplary embodiment illustrated in FIG. 4A.

Please refer to FIGS. 4A and 4B, which illustrates a possible implementation of the inventive concept that can obtain gaze angle direction using the pupil location alone to obtain the gaze direction information. In this case, the camera is located so close to the pupil that the position of the pupil alone indicates gaze direction. As shown in FIG. 4A and FIG. 4B, an eyeglass frame 400 is provided with optical arrays 420 affixed to each eyeglass frame. Inner LEDs 408 are mounted adjacent to camera 450, while the outer LEDs 413 and 415, and 417 and 419 are affixed to either side of the frame segments surrounding each eye. In this embodiment, it is also possible that the inner LEDs 408 are a partial ring. As shown in FIG. 4B, the optical array 420 consists of a camera 450, LEDs 408 on either side of the camera for providing on-axis illumination, and the LEDs 413 and 415, and 417 and 419 providing the off-axis illumination. Please note that FIG. 4B only illustrates the left-eye optical array 420 as viewed from the wearer's perspective, but one skilled in the art will be able to apply the above principles for determining the arrangement of the right-eye optical array 420. The inner LEDs 408 provides the on-axis illumination and the outer LEDs 413, 415, 417 and 419 provide the off-axis illumination. The fixed relationship between the pupils and the camera 450 allows for greater ease of implementation than the system 200 shown in FIG. 2. Please note that this system still requires calibration as the distance from the camera 450 to the pupils will differ from user to user.

By applying the threshold pixel value such that only the pupil and surface reflection information will remain in the differenced images, it is possible to implement the above system with a low resolution camera. With calibration and simple manipulation of the data, a sufficiently high performance can be achieved. The system will obviously be constrained by certain considerations such as eye motion and head velocity, but flexible sample rates and pixel sensor sensitivity can allow different implementations to be adjusted according to individual requirements. Of course, these parameters must remain within the boundaries for eye safety constraints.

In summary, by providing an optical array that captures images using at least a high-speed, low-resolution camera with a gaming motion sensor, images can be captured much more quickly than in a conventional system using retro-reflectivity. By applying a threshold pixel value to the differenced captured images, almost all background noise can be filtered out. The large amount of captured data means that gaze detection of a user can be determined via simple algorithms, thereby enabling pupil tracking, which can be implemented in a Human Interface Device.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An optical array system for performing pupil tracking using retro-reflectivity, the optical array system comprising:
   an LED array, positioned on a three-sided mounting system, comprising at least one on-axis LED and at least one off-axis LED, for illuminating pupils of a user within an active region, wherein an inner ring of LEDs is disposed on a central panel of the three-sided mounting system, a middle ring of LEDs is disposed on an inner edge of a left-hand panel and a right-hand panel, respectively, of the three-sided mounting system, and an outer ring of LEDs is disposed on an outer edge of the left-hand panel and right-hand panel, respectively, of the three-sided mounting system;
   at least a high-speed camera with a gaming motion sensor, for capturing images of the pupils illuminated by the LED array; and
   a processor, coupled to the high-speed camera, for receiving the captured images and performing processing algorithms on the captured images to isolate pupil information and thereby determine pupil presence and location within the active region.

2. The optical array system of claim 1, wherein exact locations of the LEDs of the inner ring, the middle ring and the outer ring are determined according to a calibration procedure.

3. The optical array system of claim 1, wherein a camera, an inner ring and outer ring segments of LEDs are disposed on each panel of the three-sided mounting system.

4. The optical array system of claim 1, wherein the pupil information is isolated by differencing an on-axis illuminated image and an off-axis illuminated image, and further applying a threshold pixel value to the differenced images.

5. The optical array system of claim 1, wherein a y axis of the active region is defined according to an average height of a sitting human and an x axis of the active region is defined according to an average inter-pupillary distance of a human.

6. An optical array system for performing pupil tracking using retro-reflectivity, comprising:
   an LED array comprising on-axis LEDs and off-axis LEDs, for illuminating pupils of a user within an active region;
   a first high-speed camera with a gaming motion sensor and a second high-speed camera with a gaming motion sensor, for capturing images of the pupils illuminated by the LED array; and
   a processor, coupled to the first and second high-speed cameras, for receiving the captured images and performing processing algorithms on the captured images to isolate pupil information and thereby determine pupil presence and location within the active region;
   wherein the optical array system is a pair of glasses comprising a left-eye frame, for mounting a left-eye lens; a right-eye frame for mounting a right-eye lens; a pair of arms, respectively coupled to the outermost edge of the left-eye frame and the right-eye frame; and a bridge, for joining the innermost edges of the left-eye frame and the right-eye frame; the first high-speed camera is disposed at the top and in the middle of the left-eye frame, the second high-speed camera is disposed at the top and in the middle of the right-eye frame, the off-axis LEDs are disposed at the respective outermost edges of the left-eye frame and the right-eye frame and at the respective innermost edges of the left-eye frame and the right-eye frame, and the on-axis LEDs are disposed around the first high-speed camera and the second high-speed camera.

7. A method for performing pupil tracking using retro-reflectivity, the method comprising:
   illuminating pupils of a user within an active region utilizing at least one on-axis LED and at least one off-axis LED, comprising:
       illuminating pupils of a user within the active region utilizing an inner ring of LEDs disposed on a central panel of a three-sided mounting system, a middle ring of LEDs disposed on an inner edge of a left-hand panel and a right-hand panel, respectively, of the three-sided mounting system, and an outer ring of LEDs disposed on an outer edge of the left-hand panel and right-hand panel, respectively, of the three-sided mounting system;
   providing at least a high-speed camera with a gaming motion sensor for capturing images of the illuminated pupils; and
   receiving the captured images and performing processing algorithms on the captured images to isolate pupil information and thereby determine pupil presence and location within the active region.

8. The method of claim 7, further comprising:
   determining an exact location of the LEDs of the inner ring, the middle ring and the outer ring according to a calibration procedure.

9. The method of claim 7, further comprising:
   providing a camera, an inner LED ring and outer LED ring segments on each panel of the three-sided mounting system.

10. The method of claim 7, wherein the step of isolating the pupil information comprises:
    differencing an on-axis illuminated image and an off-axis illuminated image; and
    applying a threshold pixel value to the differenced images.

11. The method of claim 7, wherein the step of illuminating pupils of a user within an active region comprises:
    defining a y axis of the active region according to an average height of a sitting human; and defining an x axis of the active region according to an average inter-pupillary distance of a human.

12. A method for performing pupil tracking using retro-reflectivity, comprising:
   providing a pair of glasses, comprising:
      a left-eye frame, for mounting a left-eye lens;
      a right-eye frame for mounting a right-eye lens;
      a pair of arms, respectively coupled to the outermost edge of the left-eye frame and the right-eye frame; and
      a bridge, for joining the innermost edges of the left-eye frame and the right-eye frame;
   disposing a first high-speed camera with a gaming motion sensor at the top and in the middle of the left-eye frame, disposing a second high-speed camera with a gaming motion sensor at the top and in the middle of the right-eye frame, disposing off-axis LEDs at the respective outermost edges of the left-eye frame and the right-eye frame and at the respective innermost edges of the left-eye frame and the right-eye frame, and disposing on-axis LEDs around the first high-speed camera and the second high-speed camera;
   illuminating pupils of a user within an active region utilizing the on-axis LEDs and the one off-axis LEDs;
   utilizing the first high-speed camera and the second high-speed camera to capture images of the illuminated pupils; and
   receiving the captured images and performing processing algorithms on the captured images to isolate pupil information and thereby determine pupil presence and location within the active region.

13. The optical array system of claim 6, wherein the pupil information is isolated by differencing an on-axis illuminated image and an off-axis illuminated image, and further applying a threshold pixel value to the differenced images.

14. The optical array system of claim 6, wherein a y axis of the active region is defined according to an average height of a sitting human and an x axis of the active region is defined according to an average inter-pupillary distance of a human.

15. The method of claim 12, wherein the step of isolating the pupil information comprises:
   differencing an on-axis illuminated image and an off-axis illuminated image; and
   applying a threshold pixel value to the differenced images.

16. The method of claim 12, wherein the step of illuminating pupils of a user within an active region comprises:
   defining a y axis of the active region according to an average height of a sitting human; and
   defining an x axis of the active region according to an average inter-pupillary distance of a human.

17. An optical array system for performing pupil tracking using retro-reflectivity, the optical array system comprising:
   an LED array comprising at least one on-axis LED and at least one off-axis LED, for illuminating pupils of a user within an active region;
   at least a low-resolution high-speed camera with a gaming motion sensor, for capturing images of the pupils illuminated by the LED array; and
   a processor, coupled to the low-resolution high-speed camera, for receiving the captured images and performing processing algorithms on the captured images to isolate pupil information and thereby determine pupil presence and location within the active region;
   wherein the pupil information is isolated by differencing an on-axis illuminated image and an off-axis illuminated image, and further applying a threshold pixel value to the differenced images, the threshold pixel value being chosen to filter out background noise of the differenced images.

18. A method for performing pupil tracking using retro-reflectivity, the method comprising:
   illuminating pupils of a user within an active region utilizing at least one on-axis LED and at least one off-axis LED;
   providing at least a low-resolution high-speed camera with a gaming motion sensor for capturing images of the illuminated pupils; and
   receiving the captured images and performing processing algorithms on the captured images to isolate pupil information and thereby determine pupil presence and location within the active region, comprising:
      differencing an on-axis illuminated image and an off-axis illuminated image; and
      applying a threshold pixel value to the differenced images;
   wherein the threshold pixel value is chosen to filter out background noise of the differenced images.

* * * * *